United States Patent [19]

Mahurkar et al.

[11] Patent Number: 5,221,255

[45] Date of Patent: Jun. 22, 1993

[54] REINFORCED MULTIPLE LUMEN CATHETER

[76] Inventors: Sakharam D. Mahurkar; Smriti S. Mahurkar, both of 6171 N. Sheridan Rd., #1112, Chicago, Ill. 60660

[21] Appl. No.: 776,873

[22] Filed: Oct. 16, 1991

Related U.S. Application Data

[63] Continuation of Ser. No. 463,285, Jan. 10, 1990, abandoned.

[51] Int. Cl.⁵ .............................................. A61M 5/00
[52] U.S. Cl. ...................................... 604/43; 604/282
[58] Field of Search ............................. 604/43–45, 604/264, 280, 281, 282

[56] References Cited

U.S. PATENT DOCUMENTS

| | | | |
|---|---|---|---|
| Re. 31,873 | 4/1985 | Howes . | |
| D. 250,349 | 11/1978 | McFarlane . | |
| D. 254,444 | 3/1980 | Levine . | |
| 256,590 | 4/1882 | Pfarre . | |
| D. 256,617 | 8/1980 | Clemens . | |
| D. 272,651 | 2/1984 | Mahurkar . | |
| 390,177 | 9/1883 | Lee . | |
| 701,075 | 5/1902 | McCully . | |
| 998,339 | 7/1911 | Hollins . | |
| 1,045,326 | 11/1912 | Ruflin . | |
| 1,093,538 | 4/1914 | Clough . | |
| 1,290,647 | 1/1919 | Nyvall . | |
| 1,922,084 | 8/1933 | Gerow . | |
| 2,175,726 | 10/1939 | Gebauer . | |
| 2,230,218 | 2/1941 | Asche . | |
| 2,234,961 | 3/1941 | Canada . | |
| 2,409,343 | 10/1946 | Curtis . | |
| 2,473,742 | 6/1949 | Auzin . | |
| 2,474,665 | 6/1949 | Guarino . | |
| 2,564,977 | 8/1951 | Hsi Hu . | |
| 2,590,895 | 4/1952 | Scarpellino . | |
| 2,625,932 | 1/1953 | Salisbury . | |
| 2,716,983 | 9/1955 | Windischman et al. . | |
| 2,819,718 | 1/1958 | Goldman . | |
| 2,930,378 | 3/1960 | Buyers . | |
| 2,936,761 | 5/1960 | Snyder | 604/282 |
| 3,042,045 | 7/1962 | Sheridan . | |
| 3,175,554 | 3/1965 | Stewart . | |
| 3,314,430 | 4/1967 | Alley et al. . | |
| 3,324,853 | 6/1967 | Czorny et al. . | |
| 3,324,854 | 6/1967 | Weese . | |
| 3,331,371 | 7/1967 | Rocchi et al. . | |
| 3,359,974 | 12/1967 | Khalil . | |
| 3,394,705 | 7/1968 | Abramson . | |
| 3,435,826 | 1/1969 | Fogarty . | |
| 3,437,088 | 4/1969 | Bielinski . | |
| 3,448,739 | 6/1969 | Stark et al. . | |
| 3,452,756 | 7/1969 | Harautuneian . | |
| 3,459,188 | 7/1965 | Roberts . | |
| 3,463,152 | 8/1969 | Sorenson . | |
| 3,467,101 | 9/1969 | Fogarty et al. . | |
| 3,543,758 | 12/1970 | McWhorter . | |
| 3,543,759 | 12/1970 | McWhorter . | |
| 3,550,591 | 12/1970 | MacGregor . | |
| 3,556,161 | 1/1971 | Roberts | 138/141 |
| 3,566,874 | 3/1971 | Sheperd et al. . | |
| 3,593,713 | 7/1971 | Bogoff et al. . | |
| 3,599,620 | 8/1971 | Balin . | |
| 3,612,050 | 4/1969 | Sheridan . | |

(List continued on next page.)

Primary Examiner—Stephen C. Pellegrino
Assistant Examiner—Ralph A. Lewis
Attorney, Agent, or Firm—Arnold, White & Durkee

[57] ABSTRACT

A dual-lumen catheter comprises an elongated cylindrical tube made of silicone and having an internal septum extending along the length thereof to form a pair of longitudinal lumens. A hollow conical tip is formed on the distal end of the tube with the outside surface of the conical tip merging smoothly with the outside surface of the tube, and the inside surface of the conical tip merging smoothly with the inside surface of one of the lumens.

The distal end of the other lumen is longitudinally spaced from the distal end of the tip. A reinforcing member is located inside the tube and extends along the length of the tube. The reinforcing member is made of a material which is substantially stiffer than the material of the tube so that the catheter can be advanced against a resistance by the applications of force to the proximal end of the catheter.

34 Claims, 7 Drawing Sheets

U.S. PATENT DOCUMENTS

| | | | |
|---|---|---|---|
| 3,634,924 | 1/1972 | Blake et al. | |
| 3,683,908 | 8/1972 | Michael et al. | |
| 3,726,281 | 4/1973 | Norton et al. | |
| 3,746,003 | 7/1973 | Blake et al. | |
| 3,756,234 | 9/1973 | Kopp | |
| 3,771,527 | 11/1973 | Ruisi | |
| 3,774,605 | 11/1973 | Jewett | |
| 3,799,172 | 3/1974 | Szpur | |
| 3,804,097 | 4/1974 | Rudie | |
| 3,823,720 | 7/1974 | Tribble | |
| 3,828,767 | 8/1974 | Spiroff | |
| 3,830,234 | 8/1974 | Kopp | |
| 3,875,938 | 4/1975 | Mellor | |
| 3,885,567 | 5/1975 | Ross | |
| 3,896,815 | 7/1975 | Fettel et al. | |
| 3,978,863 | 9/1976 | Fettel et al. | |
| 4,004,588 | 1/1977 | Alexander | |
| 4,016,879 | 4/1977 | Mellor | |
| 4,027,668 | 6/1977 | Dunn | |
| 4,037,599 | 7/1977 | Raulerson | |
| 4,057,065 | 11/1977 | Thow | |
| 4,072,146 | 2/1978 | Howes | |
| 4,096,860 | 6/1978 | McLaughlin | |
| 4,098,275 | 6/1978 | Consalvo | |
| 4,099,528 | 7/1978 | Sorenson et al. | |
| 4,100,246 | 7/1978 | Frisch | |
| 4,116,068 | 9/1978 | Megahed | |
| 4,134,402 | 1/1979 | Mahurkar | |
| 4,144,884 | 3/1979 | Tersteegen et al. | |
| 4,168,703 | 9/1979 | Kenigsberg | |
| 4,180,068 | 12/1979 | Jacobsen et al. | |
| 4,202,332 | 5/1980 | Tersteegen et al. | |
| 4,203,436 | 5/1980 | Grimsrud | |
| 4,217,895 | 8/1980 | Sagae et al. | |
| 4,257,416 | 3/1981 | Prager | |
| 4,270,535 | 7/1981 | Bogue et al. | |
| 4,314,555 | 2/1982 | Sagae | |
| 4,336,636 | 6/1982 | Leeke et al. | |
| 4,385,631 | 5/1983 | Uthmann | 604/284 |
| 4,403,983 | 3/1983 | Edelman et al. | 604/43 |
| 4,403,985 | 9/1983 | Boretos | 604/53 |
| 4,406,656 | 9/1983 | Hattler et al. | 604/280 |
| 4,419,095 | 12/1983 | Nerbergall et al. | 604/96 |
| 4,443,333 | 4/1984 | Mahurkar | 210/87 |
| 4,451,252 | 5/1984 | Martin | 604/43 |
| 4,452,473 | 6/1984 | Ruschke | |
| 4,473,369 | 9/1984 | Lueders et al. | 604/244 |
| 4,484,585 | 11/1984 | Baier | |
| 4,493,696 | 5/1985 | Uldell | 604/43 |
| 4,535,770 | 8/1985 | Lemole | |
| 4,543,087 | 9/1985 | Sommercorn et al. | 604/43 |
| 4,547,193 | 10/1985 | Rydell | 604/282 |
| 4,568,329 | 2/1986 | Mahurkar | 604/43 |
| 4,583,968 | 4/1986 | Mahurkar | 604/43 |
| 4,592,749 | 6/1986 | Ebling et al. | 604/283 |
| 4,619,643 | 10/1986 | Bai | 604/43 |
| 4,623,327 | 11/1986 | Mahurkar | 604/4 |
| 4,626,240 | 12/1986 | Edelman et al. | 604/43 |
| 4,643,711 | 2/1987 | Bates | 604/43 X |
| 4,661,110 | 4/1987 | Fortier et al. | 604/256 |
| 4,676,229 | 6/1987 | Krasnicki et al. | 604/282 |
| 4,682,978 | 7/1987 | Martin | 604/43 |
| 4,692,141 | 9/1987 | Mahurkar | 604/43 |
| 4,706,670 | 11/1987 | Anderson | 604/282 |
| 4,723,948 | 2/1988 | Clark et al. | 604/283 |
| 4,753,640 | 6/1988 | Nichols et al. | 604/247 |
| 4,772,268 | 9/1988 | Bates | 604/174 |
| 4,795,439 | 1/1989 | Guest | 604/280 |
| 4,822,345 | 4/1989 | Danforth | 604/282 |
| 4,827,921 | 5/1989 | Rugheimer | |
| 4,894,057 | 1/1990 | Howes | 604/280 |
| 4,995,865 | 2/1991 | Gahara et al. | 604/43 |

FOREIGN PATENT DOCUMENTS

| | | | |
|---|---|---|---|
| 834211 | 2/1976 | Belgium | |
| 1092927 | 1/1981 | Canada | 604/43 |
| 50089 | 8/1982 | Canada | |
| 1150122 | 7/1983 | Canada | |
| 1193508 | 4/1984 | Canada | |
| 1167727 | 5/1984 | Canada | |
| 36642 | 9/1981 | European Pat. Off. | 604/43 |
| 0079719 | 11/1982 | European Pat. Off. | |
| 79719 | 5/1983 | European Pat. Off. | |
| 333308 | 2/1989 | European Pat. Off. | |
| 322225 | 6/1989 | European Pat. Off. | |
| 935625 | 11/1955 | Fed. Rep. of Germany | |

(List continued on next page.)

OTHER PUBLICATIONS

McIntosh et al., "Double Lumen Catheter," J.A.M.A., Feb. 21, 1959 pp. 137/835-138/836.

Dorland's Illustrated Medical Dictionary, 25th Ed., W. B. Saudners Co., Philadelphia, 1974, p. 274.

Tsuchida et al., "Single Two-Lumen Cannula Dialysis", Toboku Journal Exp. Med., 1974, pp. 114, 159-101.

(List continued on next page.)

FOREIGN PATENT DOCUMENTS

| | | |
|---|---|---|
| 2259865 | 6/1974 | Fed. Rep. of Germany . |
| 3010841 | 2/1980 | Fed. Rep. of Germany . |
| 19346 | 6/1982 | Fed. Rep. of Germany . |
| 592193 | 4/1925 | France . |
| 1285953 | 7/1962 | France . |
| 1508959 | 1/1968 | France . |
| 2285148 | 4/1976 | France . |
| 2297640 | 8/1976 | France . |
| 821344 | 4/1982 | France . |
| 2530958 | 2/1984 | France . |
| 5588771 | 7/1980 | Japan . |
| 8404043 | 10/1984 | PCT Int'l Appl. . |
| 1017315 | 5/1983 | U.S.S.R. . |
| 688450 | 3/1952 | United Kingdom . |
| 1419702 | 12/1975 | United Kingdom . |
| 1503469 | 10/1976 | United Kingdom . |
| 1006219 | 3/1983 | United Kingdom . |
| 04664 | 12/1984 | World Int. Prop. O. . |

OTHER PUBLICATIONS

Tsuchida et al., "Design of a Two-Lumen-Piercing Needle That Is Capable of Carrying Out Dialysis By Single Puncture", Journal of The Urological Society of Japan, vol. 65 (12), 1974, pp. 805-807.

Brenner & Rector, The Kidney, vol. III, W. B. Saunders Co., Philadelphia, 1976, p. 164.

ASAIO Abstracts, vol. 5, 22nd Annual Meeting, San Francisco, Calif., Apr. 1-3, 1976, p. 164.

Kaplan et al., "A Co-Axial Dual Flow Catheter/Cannula for Single Puncture Dialysis", Dialysis & Transplantation, Dec./Jan. 1977, pp. 38-40, 42, 84.

"Terumo Cozxial Dual Flow Catheter", Terumo American, Inc. Apr., 1979 (two pages).

Reus et al., "Double-Lume Catheter in Extracorporeal Hemodialysis" Archives of Internal Medicine, vol. 113, Apr. 1964.

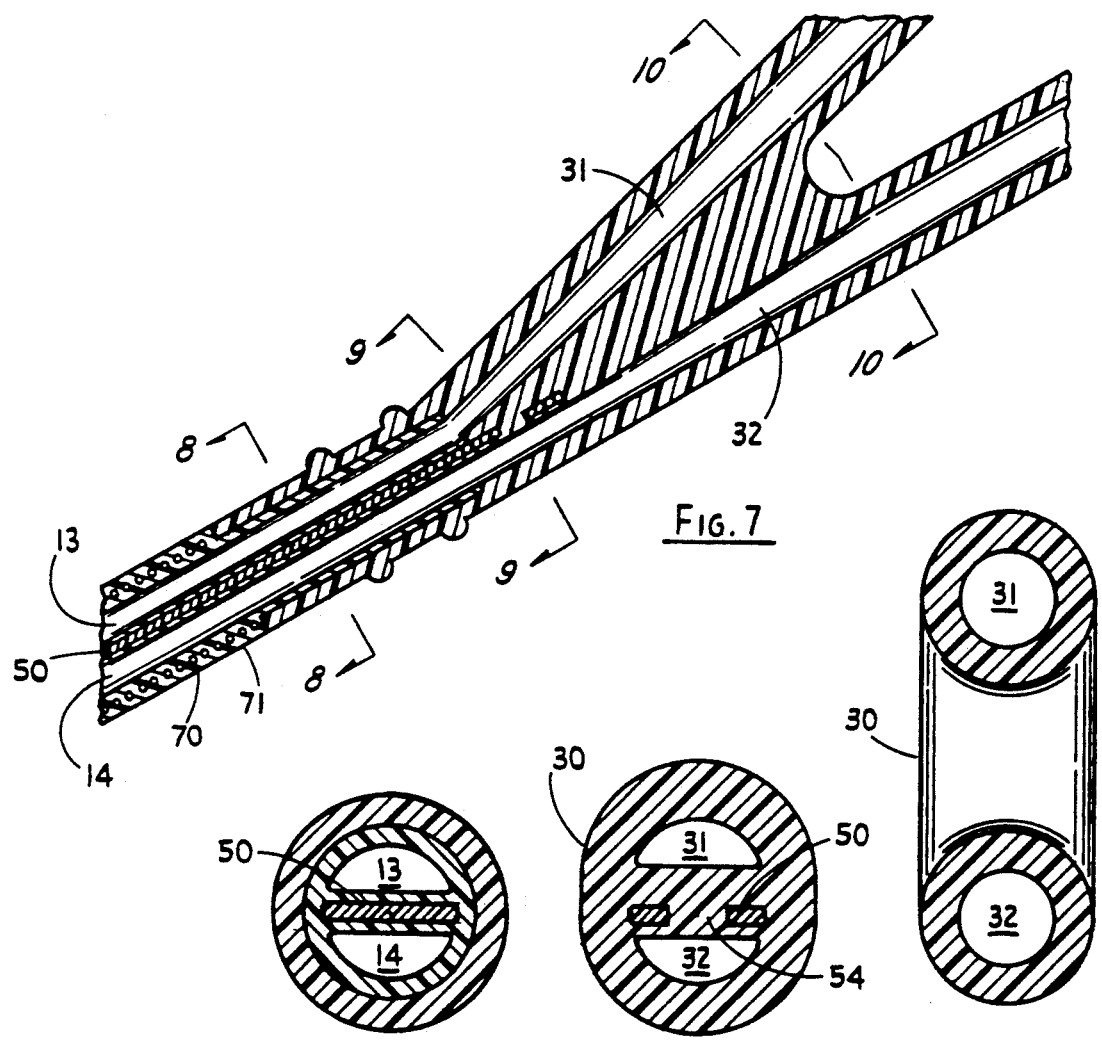
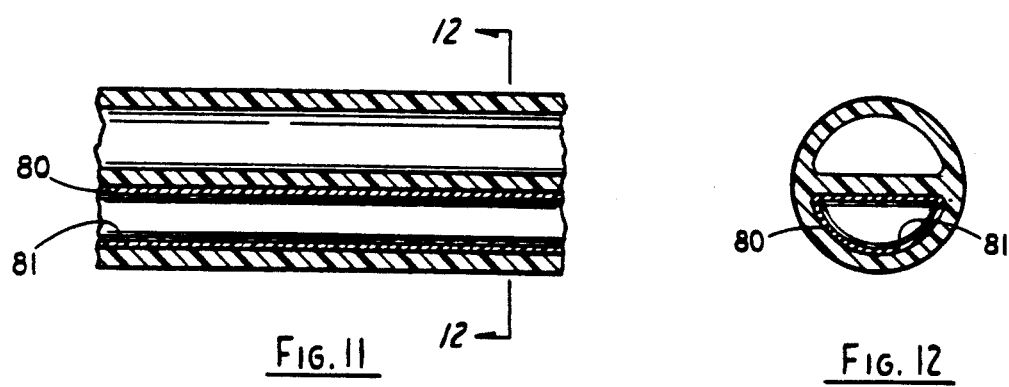

REINFORCED MULTIPLE LUMEN CATHETER

This application is a continuation of application Ser. No. 463,285, filed Jan. 10, 1990 now abandoned.

FIELD OF THE INVENTION

The present invention relates generally to multiple-lumen catheters for use in medical applications such as hemodialysis where fluids must flow simultaneously to and from a patient. This invention relates particularly to such catheters which are intended to remain inserted in patients for prolonged periods of treatment, such as a month or more.

BACKGROUND OF THE INVENTION

Dual-lumen catheters have come into widespread use for extracorporeal blood purification procedures such as hemodialysis. Blood is withdrawn from the patient through one of the lumens of the catheter and supplied to a hemodialysis unit where the blood is purified, and the resulting purified blood is then returned to the patient through the other lumen of the catheter. Examples of such catheters are shown in U.S. Pat. Nos. 4,134,402; 4,583,968; 4,568,329 and 4,692,141.

At the present time most dual-lumen catheters used for hemodialysis are made of either polyurethane or silicone rubber. The polyurethane catheters are sufficiently rigid that they can be introduced into a patient's vein percutaneously, without surgery, but such catheters tend to be incompatible with the human body when left in place for long periods of time (e.g., a month or more). The silicone catheters can be left in place indefinitely without allergic reactions or traumatic problems in most patients, but the initial insertion of such catheters usually requires surgical intervention; the soft, pliable, elastic properties of the silicone which contribute to its compatibility with the human body are the same properties that make it difficult or impossible to insert such catheters percutaneously into a patient's vein.

SUMMARY OF THE INVENTION

It is a primary object of this invention to provide an improved multiple-lumen catheter which can be made of silicone or other relatively soft, elastic materials which are unlikely to be rejected by the body, and thus can be used for long-term applications, and yet can be inserted into a patient without surgery.

It is another important object of this invention to provide an improved multiple-lumen catheter which can be made of silicone, and yet can be inserted with the use of a needle, guide wire and peel-apart sheath, i.e., without surgical intervention.

A further object of this invention is to provide an improved multiple-lumen catheter which ca be adapted for long-term use in femoral veins with little or no danger of infection. In this connection, a related object of the invention is to provide such an improved catheter which permits the access site for the catheter to be located above the thighs of the patient.

Yet another object of this invention is to provide an improved method of implanting a multiple-lumen catheter in a femoral vein.

A still further object of the invention is to provide an improved multiple lumen catheter which resists kinking, even when bent at angles of less than 90°.

In accordance with the present invention, the foregoing objectives are realized by providing a multiple-lumen catheter comprising an elongated cylindrical tube made of a soft elastic material and having an internal septum extending along the length thereof to form a pair of longitudinal lumens; and a reinforcing member extending along the full length of at least one of the lumens for transmitting forces applied to the proximal end of the tube to the distal end of the tube. In a preferred embodiment, the reinforcing member is embedded in the septum and is made of a material which is substantially stiffer than the material of the tube so that the catheter can be advanced against a resistance by the application of force to the proximal end of the catheter. The reinforcing member also avoids deformation and/or collapse of one or more of the lumens when a pressure gradient exists across the septum.

This invention also provides a method of introducing a dual-lumen catheter into a femoral vein of a patient for long-term use, the method comprising the steps of making a cutaneous tunnel on the abdomen of the patient, beginning above the inguinal ligament and extending downwardly to a point on the thigh that is proximate the femoral vein; passing a dual-lumen catheter downwardly through the tunnel; and then bending the catheter and inserting it upwardly into the femoral vein, in the direction of blood flow within the vein, the catheter being bent in a generally U-shaped configuration between the lower end of the tunnel and the point of access to the femoral vein, the U-bend being reinforced by a spiral winding of reinforcing material.

In a modified embodiment of the invention, the cylindrical tube has a pair of orthogonal flat internal dividers extending along the interior of the tube for dividing the interior into three lumens extending along the length of the tube, one of the lumens having a D-shaped transverse cross section. The orthogonal dividers form a T-shaped septum which resists kinking of the catheter along orthogonal transverse planes.

BRIEF DESCRIPTION OF THE DRAWINGS

Other objects and advantages of the invention will become apparent upon reading the following detailed description and upon reference to the accompanying drawings, in which:

FIG. 7 is an enlarged horizontal section taken through the center of the y-shaped hub of the catheter of FIG. 1;

FIG. 8 is a section taken generally along line 8—8 in FIG. 7;

FIG. 9 is a section taken generally along line 9—9 in FIG. 7;

FIG. 10 is a section taken generally along line 10—10 in FIG. 7;

FIG. 11 is a fragmentary longitudinal section through the main body portion of a dual lumen catheter, normal to the septum, containing a modified reinforcing member;

FIG. 12 is a section taken generally along line 12—12 in FIG. 11;

Figure 1:
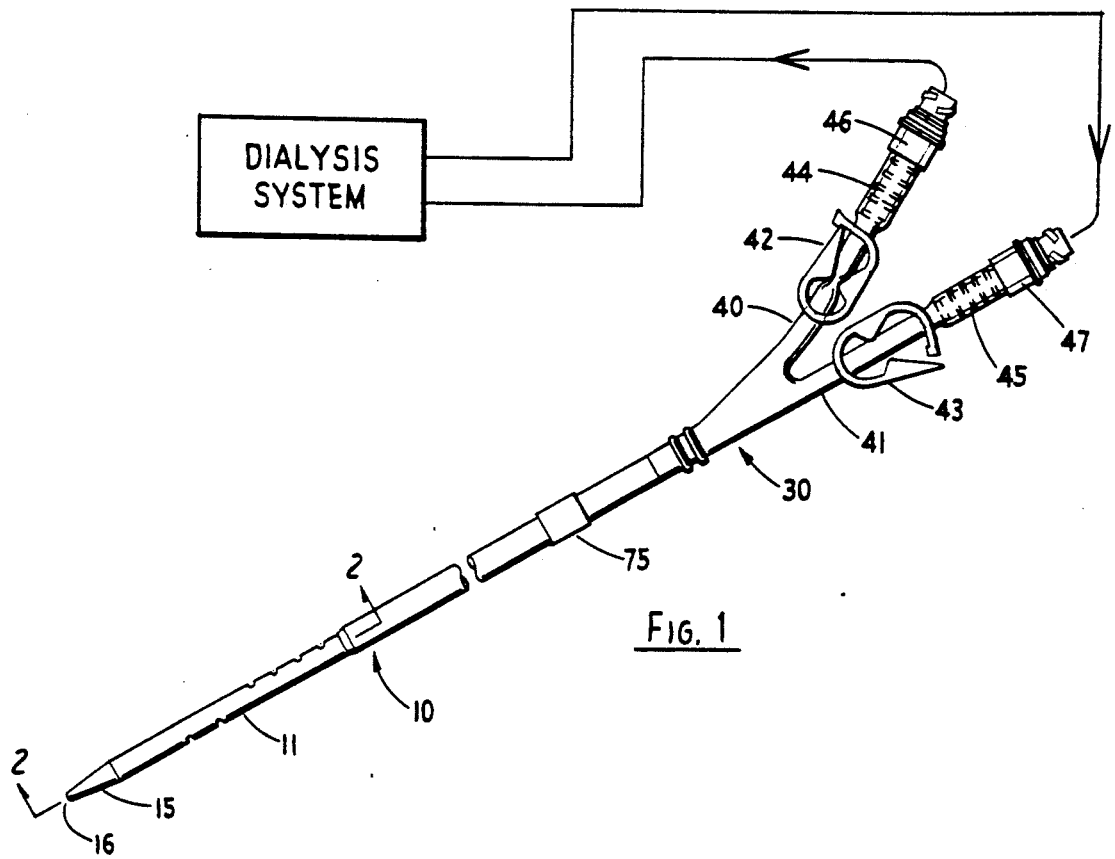
FIG. 1 is a perspective view of a dual-lumen hemodialysis catheter assembly embodying the present invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DESCRIPTION OF THE PREFERRED EMBODIMENTS

Figure 2:
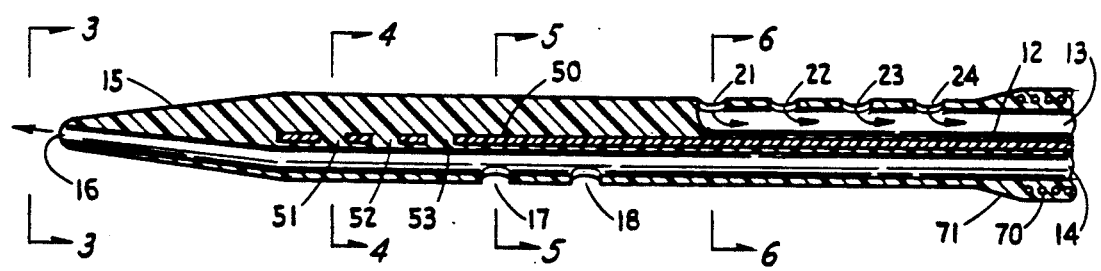
FIG. 2 is a enlarged longitudinal section taken along a diameter of the distal portion of the catheter of FIG. 1, perpendicular to the septum inside the catheter, as generally illustrated by line 2—2 in FIG. 1.
Figure 6:
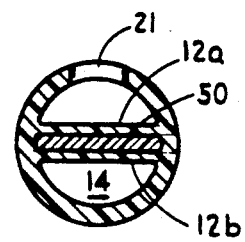
FIG. 6 is a section taken generally along line 6—6 in FIG. 2.
Figure 13:
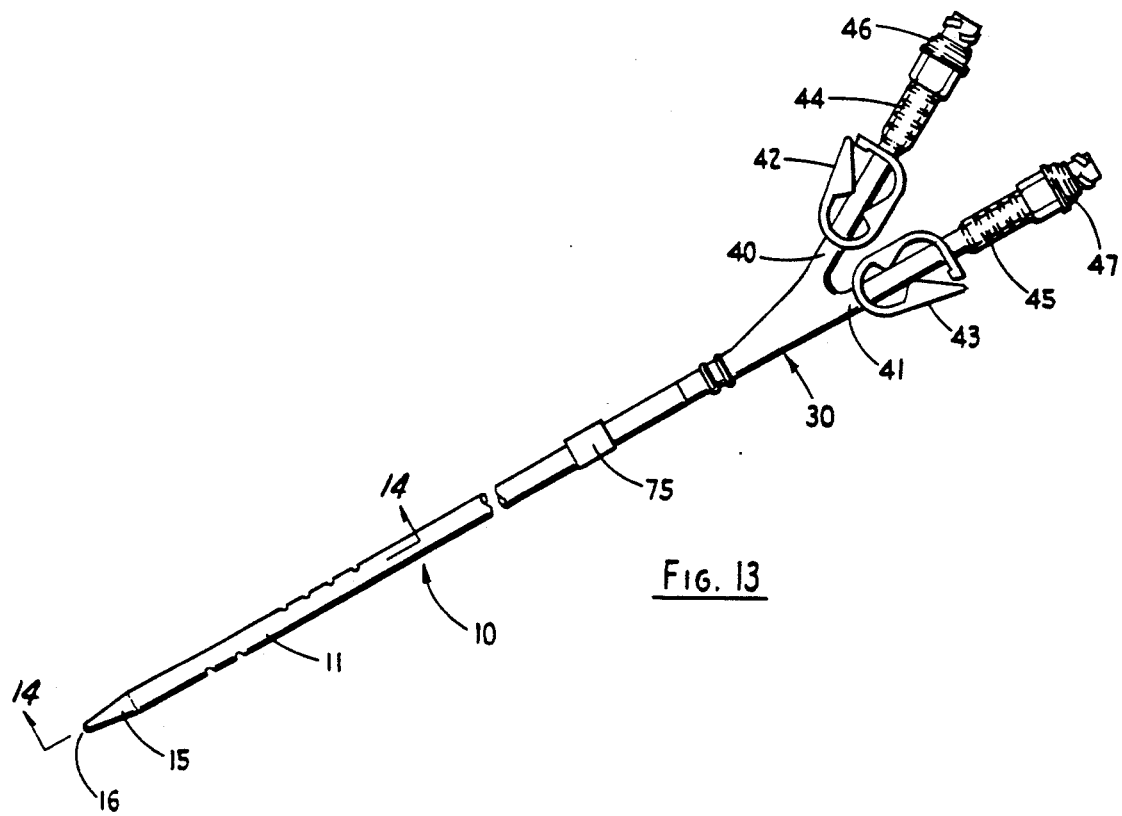
FIG. 13 is a perspective view of a modified dual-lumen hemodialysis catheter assembly embodying the invention.
Figure 14:
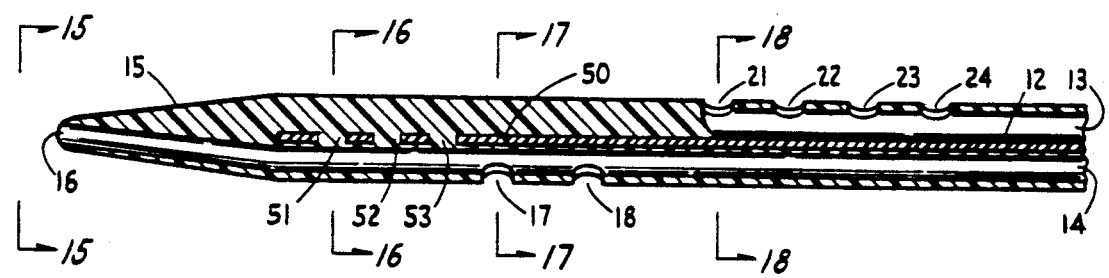
FIG. 14 is an enlarged longitudinal section taken generally along line 14—14 in FIG. 13.
Figure 15:
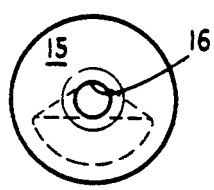
FIG. 15 is an end elevation taken at the distal end of the catheter portion shown in FIG. 14, as illustrated by line 15—15 in FIG. 14.
Figure 16:
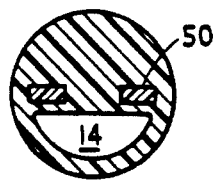
FIG. 16 is a section taken generally along line 16—16 in FIG. 14.
Figure 17:
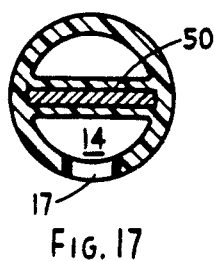
FIG. 17 is a section taken generally along line 17—17 in FIG. 14.
Figure 18:
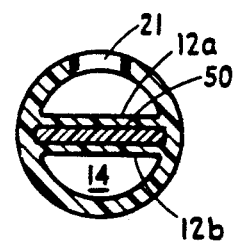
FIG. 18 is a section taken generally along line 18—18 in FIG. 14.
Figure 19:
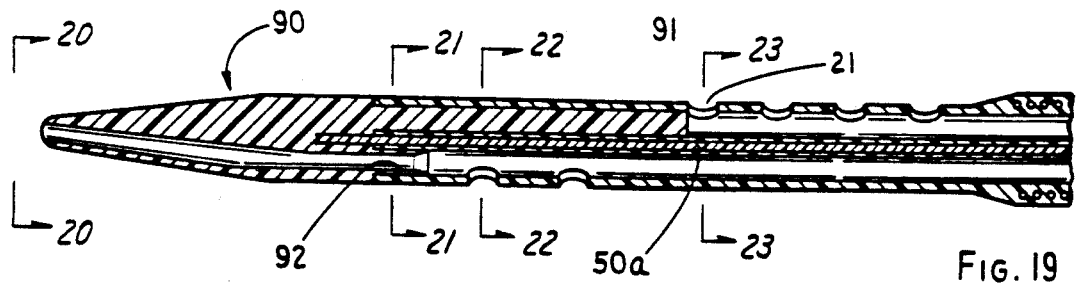
FIG. 19 is a longitudinal section similar to FIG. 2 but showing a modified embodiment of the invention.
Figure 20:
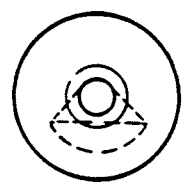
FIG. 20 is an end elevation taken at the distal end of the catheter portion shown in FIG. 19, as illustrated by line 20—20 in FIG. 19.
Figure 21:
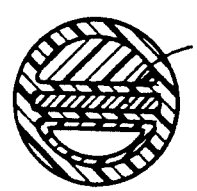
FIG. 21 is a section taken generally along line 21—21 in FIG. 19.
Figure 22:
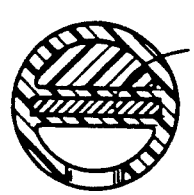
FIG. 22 is a section taken generally along line 22—22 in FIG. 19
Figure 23:
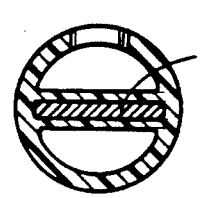
FIG. 23 is a section taken generally along line 23—23 in FIG. 19.
Figure 24:
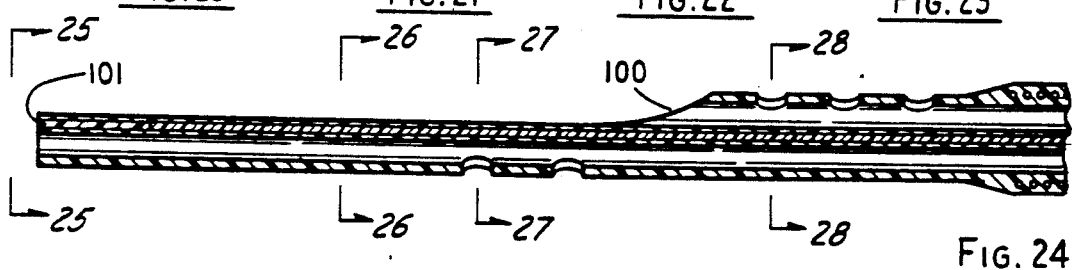
FIG. 24 is a longitudinal section similar to FIG. 2 but showing another modified embodiment of the invention.
Figure 25:
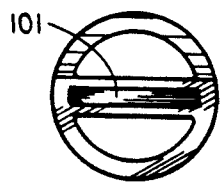
FIG. 25 is an end elevation taken at the distal end of the catheter portion shown in FIG. 24, as illustrated by line 25—25 in FIG. 24.
Figure 26:
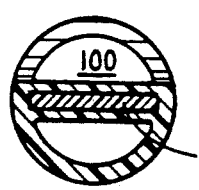
FIG. 26 is a section taken generally along line 26—26 in FIG. 24.
Figure 27:
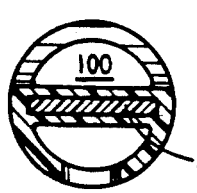
FIG. 27 is a section taken generally along line 27—27 in FIG. 24.
Figure 28:
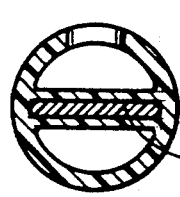
FIG. 28 is a section taken generally along line 28—28 in FIG. 24.
Figure 29:
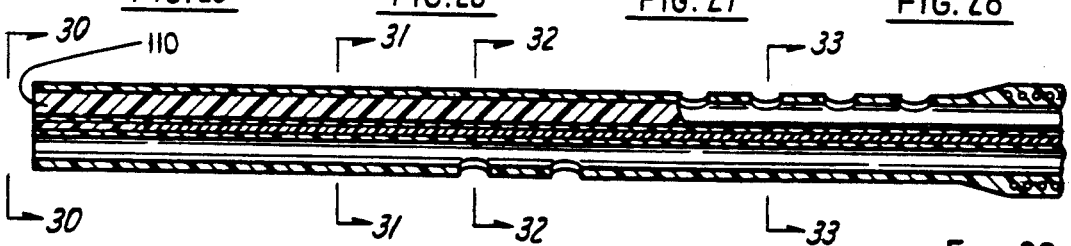
FIG. 29 is a longitudinal section similar to FIG. 2 but showing a further modified embodiment of the invention.
Figure 30:
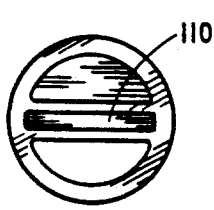
FIG. 30 is an end elevation taken at the distal end of the catheter portion shown in FIG. 29, as illustrated by line 30—30 in FIG. 29.
Figure 31:
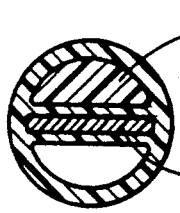
FIG. 31 is a section taken generally along line 31—31 in FIG. 29.
Figure 32:
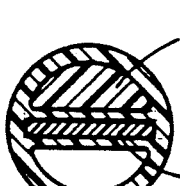
FIG. 32 is a section taken generally along line 32—32 in FIG. 29.
Figure 33:
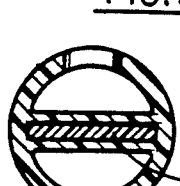
FIG. 33 is a section taken generally along line 33—33 in FIG. 29.
Figure 34:
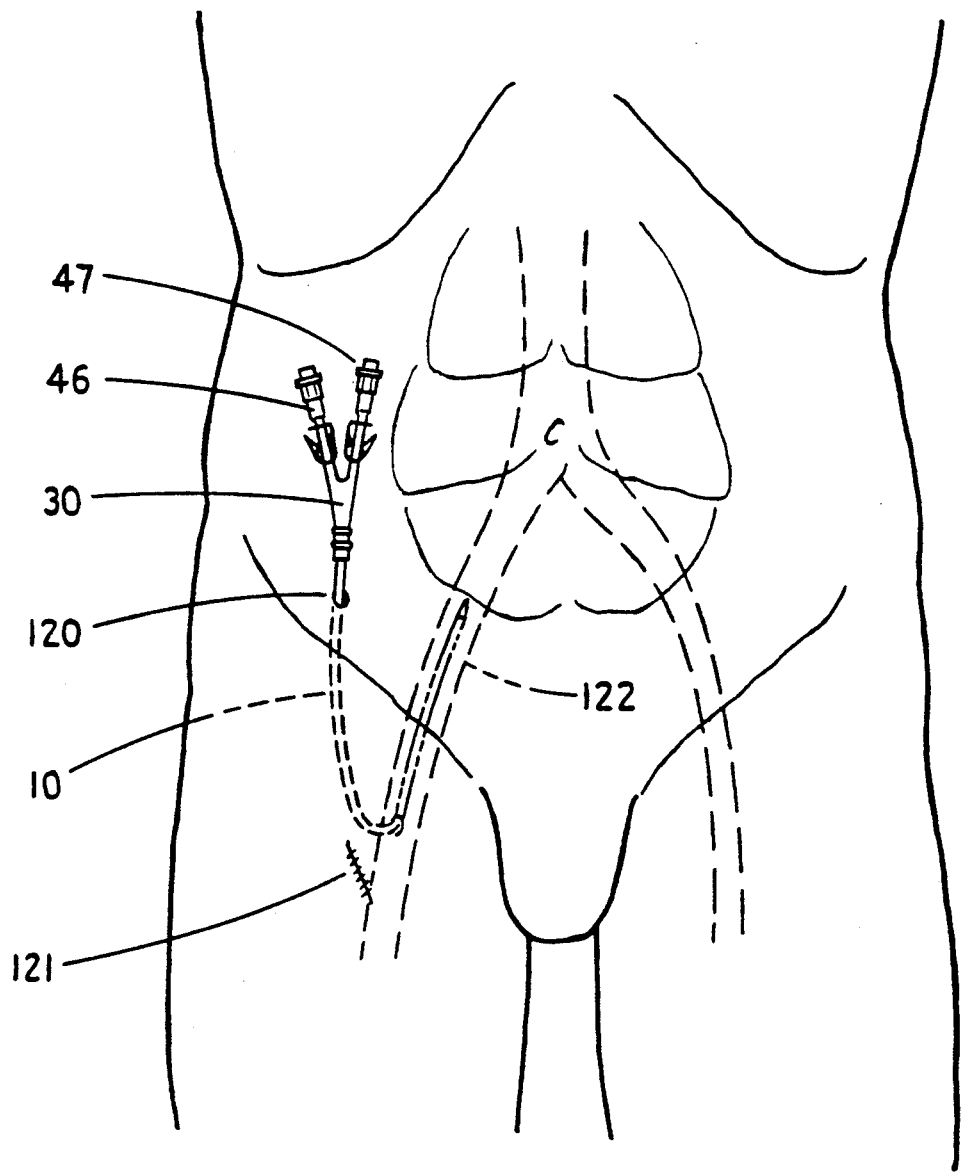
FIG. 34 is a front elevation of the abdominal portion of a patient having the catheter of FIG. 1 implanted in a femoral vein via a subcutaneous tunnel.
Figure 35:
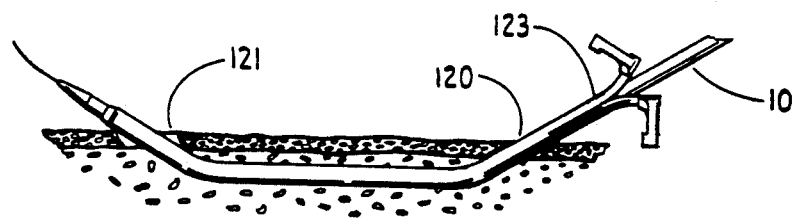
FIG. 35 is an enlarged section illustrating the cutaneous tunnel in the patient of FIG. 34 with a guide-wire, catheter and peel-apart sheath inserted therethrough.
Figure 36:
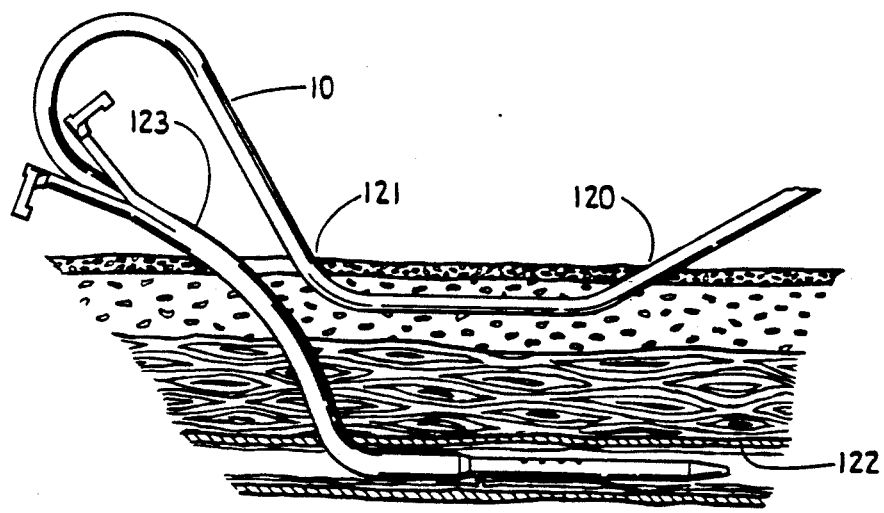
FIG. 36 is an enlarged section illustrating a catheter extending through the cutaneous tunnel, and then through a second peel-apart sheath extending into the femoral vein, in the patient of FIG. 34.
Figure 37:
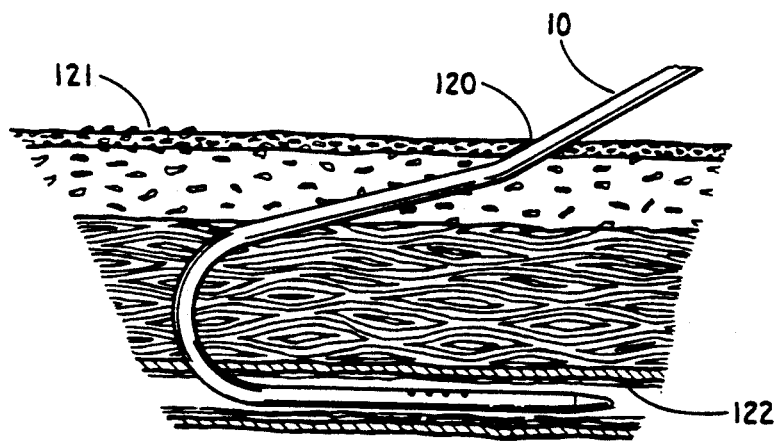
FIG. 37 is an enlarged section illustrating the catheter implanted in the femoral vein of the patient of FIG. 34.
Figure 38:
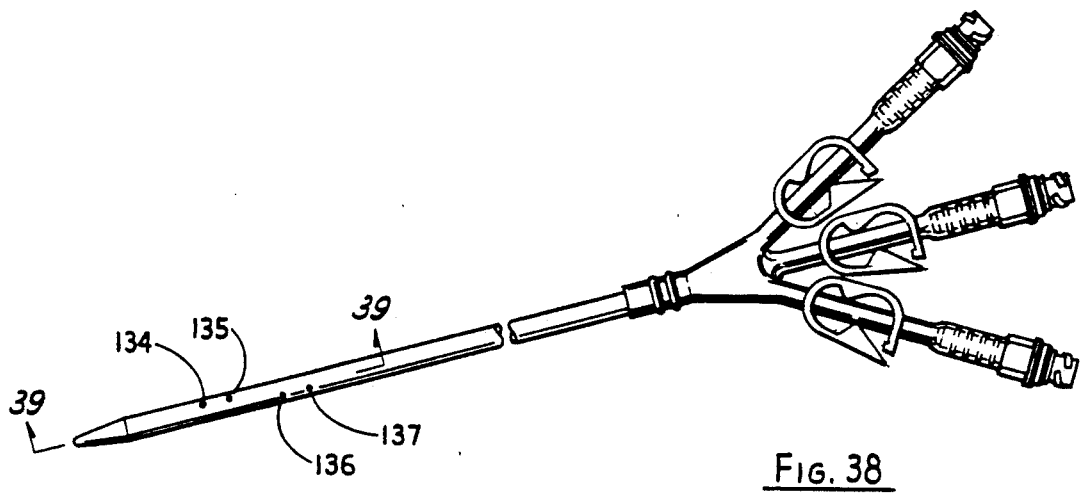
FIG. 38 is a perspective view of a triple-lumen hemodialysis catheter assembly embodying the present invention.
Figure 39:
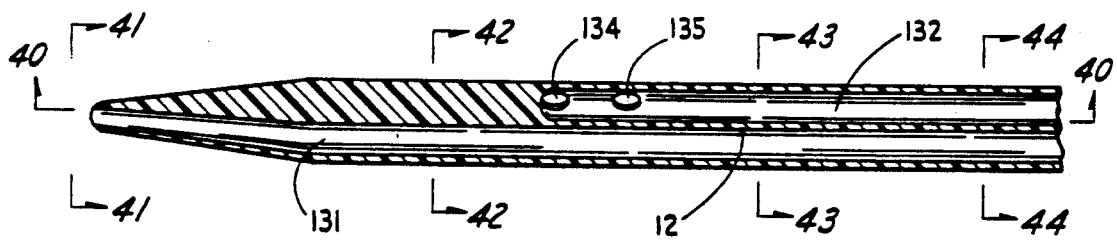
FIG. 39 is an enlarged longitudinal section taken generally along line 39—39 in FIG. 38.
Figure 40:
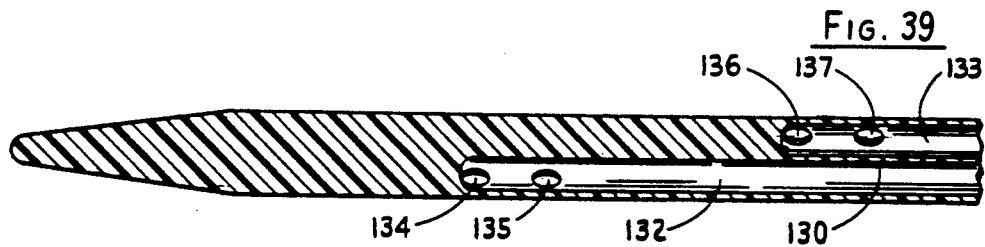
FIG. 40 is an enlarged longitudinal section taken generally along line 40—40 in FIG. 39.
Figure 41:
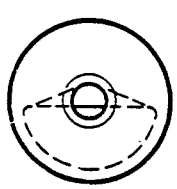
FIG. 41 is an end elevation taken at the distal end of the catheter portion shown in FIG. 39 as illustrated by line 41—41 in FIG. 39.
Figure 42:
FIG. 42 is a section taken generally along line 42—42 in FIG. 39.
Figure 43:
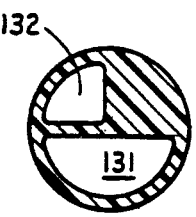
FIG. 43 is a section taken generally along line 43—43 in FIG. 39.
Figure 44:
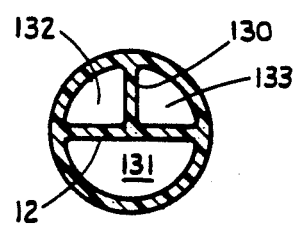
FIG. 44 is a section taken generally along line 44—44 in FIG. 39.

Turning now to the drawings and referring first to FIGS. 1-6, there is shown a dual-lumen hemodialysis catheter 10 of the general type described in Mahurkar U.S. Pat. No. 4,583,968, issued Apr. 22, 1986, for "Smooth Bore Double Lumen Catheter". This catheter 10 has a cylindrical body portion 11 made of silicone. The body portion 11 is hollow except for a flat, longitudinal, diametral septum comprising webs 12a-12b which divide the interior of the hollow cylinder into two parallel lumens 13 and 14, each having a D-shaped cross section (FIGS. 2 and 6). As illustrated by the arrows in FIG. 2, the lumen 13 is the blood-intake lumen, and the lumen 14 is the blood-return lumen.

Figure 3:
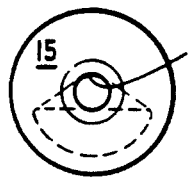
FIG. 3 is an end elevation taken at the distal end of the catheter portion shown in FIG. 2, as illustrated by line 3—3 in FIG. 2.

At the distal end of the catheter, the exterior surface of the cylinder 11 merges into a smoothly tapered conical tip 15. On the inside, the blood return lumen 14 extends longitudinally all the way through the tip 15, bending slightly as it passes through the tip so that it opens at 16 near the center of the distal end of the conical tip, as can be seen in FIGS. 2 and 3. Within the tip 15, the cross-sectional shape of the lumen 14 gradually changes from D-shaped at the proximal end of the tip 15 (see FIG. 4) to circular at the distal end of the tip (see FIG. 3). The transition from D to circular is illustrated by the broken lines in FIG. 3.

In addition to the opening 16 at the distal end of the blood-return lumen 14, a pair of apertures 17 and 18 are formed in the side wall of the return lumen. These apertures 17 and 18, which are spaced longitudinally away from the distal opening 16 toward the proximal end of the catheter, ensure the flow of blood through the return lumen 14 even in situations where the distal opening 16 might become wholly or partially blocked. The area of the apertures 16, 17 and 18 is preferably at least equal to the transverse cross-sectional area of the return lumen 14.

In order to provide a longitudinal spacing between the distal openings of the two lumens 13 and 14, the blood-intake lumen 13 is terminated at an opening 21 in the side wall of the catheter. Additional openings 22-24 spaced longitudinally from the opening 21 permit blood to enter the lumen 13 freely without excessive vacuum in the event of a blockage of the opening 21 against the wall of the vein into which the catheter 10 is inserted.

At the proximal end of the catheter 10, the two D-shaped lumens 13 and 14 open into a Y-shaped connector or hub 30 which forms two internal passageways 31 and 32 (see FIGS. 7-10) communicating with the proximal ends of the catheter lumens. As can be seen in FIGS. 7 and 9, the distal ends of the hub passageways 31 and 32 are D-shaped so that they form extensions of the catheter lumens 13 and 14, respectively. The passageways 31 and 32 diverge from each other and assume a circular cross section (see FIG. 10) as they extend toward the proximal end of the hub, and they also increase in cross-sectional area, as can be seen in FIGS. 7 and 10. The hub 30 is preferably molded in place on the end of the catheter, using mold inserts to form the hub passageways 31 and 32. Alternatively, the walls of the catheter lumens may be expanded at the proximal end of the catheter to fit over the corresponding portions of a preformed hub 30 with the inside walls of the catheter lumens being bonded to the mating walls of the hub 30.

To facilitate connection of the catheter hub 30 to the conventional tubes leading to a dialysis unit, and also to accommodate a pair of clamps for opening and closing the blood intake and return passageways the hub 30 forms a pair of extension tubes 40 and 41 (FIG. 1). These extension tubes 40 and 41 are long enough to receive a pair of conventional clamps 42 and 43 for opening and closing the respective tubes. The extension tubes 40 and 41 are relatively soft and flexible, so that they can be easily manipulated and also easily closed by the pressure of the clamps 42 and 43. The clamps 42 and 43 serve as on-off valves for controlling the flow of blood between the catheter and the dialysis unit. At the proximal end of the hub 30, the hub passageways 31 and 32 open onto a pair of ferrules 44 and 45 formed as integral parts of luer connectors 46 and 47. The luer connectors serve as coupling means for coupling the proximal ends of the extension tubes to the flexible tubes leading to the extracorporeal blood treatment unit.

In accordance with one aspect of the present invention, a reinforcing member is embedded in the septum 12 and extends along the full length of the intake lumen 13. The reinforcing member is made of a material which is substantially stiffer than the silicone used to form the main body of the catheter, so that the catheter can be advanced against a resistance by the application of force to the proximal end of the catheter. In the illustrative embodiment of FIGS. 1-6, the reinforcing member is in the form of a flat polymeric strip 50 inserted longitudinally within a hollow septum 12. The width of the strip 50 is preferably slightly greater than the inside diameter of the silicone tube so that the strip extends slightly into the cylindrical walls of the tube.

The reinforcing strip 50 is made of a material that is stiff enough to transmit longitudinally applied forces from the proximal end of the catheter to the conical tip at the distal end of the catheter so that the catheter can be readily inserted into a patient percutaneously, i.e., without surgical intervention. One suitable material for the reinforcing strip is nylon, which provides the requisite degree of stiffness in a strip 0.135 inch wide and 0.012 inch thick.

With the reinforcing strip, a silicone catheter can be easily inserted through a peel-apart sheath. Such a sheath is typically used after a guide wire has been introduced into a patient's vein by use of an access needle. The puncture formed by the needle is subsequently dilated by a smooth plastic tip on the end of a dilator telescoped through the pull-apart sheath and inserted a short distance into the vein. The dilator is then removed, the catheter is inserted through the sheath, and finally the sheath is removed by stripping it apart along two longitudinal tear lines.

Without the reinforcing member provided by this invention, attempts to insert a silicone catheter by the technique described above have usually resulted in radial expansion of the catheter at the entry to the sheath, due to the frictional resistance of the silicone surface engaging the inside wall of the sheath. Rather than causing the catheter to slide through the sheath, the applied insertion force resulted in expansion of the soft, elastic silicone material of the catheter body against the proximal end of the sheath, thereby preventing the catheter from sliding through the sheath.

With the present invention, however, the insertion force applied to the proximal end of the catheter is transmitted by the reinforcing member to the tip of the catheter, thereby "pulling" the catheter through the sheath. That is, the relatively stiff reinforcing member provides the catheter with sufficient column strength for easy insertion through the sheath. Although presently available materials that have the stiffness needed in the reinforcing material are not suitable for long-term implantation in the human body because of incompatibility problems such as localized allergic reactions, the present invention enables the reinforcing material to be isolated from the body. Thus, in the embodiment of FIG. 1, for example, the nylon reinforcing material is surrounded by the silicone material of the hollow septum. Therefore, it is only the silicone material that comes into contact with internal body tissues or fluids.

In addition, the reinforcing member prevents collapse of one of the lumens due to the pressure differential that normally exists across the septum of a dual-lumen catheter while it is being used to withdraw blood under a negative pressure in one lumen and to return blood under a positive pressure in the other lumen. With a silicone catheter, it is possible for the septum and the outside wall of the negative-pressure lumen to collapse together, thereby closing that lumen. The reinforcing strip, however, provides sufficient rigidity to the septum to prevent such collapsing of the negative-pressure lumen. Even when the outer wall of the lumen is not reinforced, the curvature of that wall normally prevents it from being collapsed against the septum as long as the septum itself cannot be distorted substantially toward the outer wall.

The preferred method of making the catheter of FIG. 1 is to extrude the main body portion of the catheter as a cylindrical tube having a hollow septum forming webs 12a and 12b for dividing the interior of the tube into two D-shaped lumens and a central cavity for receiving the reinforcing strip 50 (see FIG. 6). The extruded tube can be cut into the desired lengths for individual catheters. The strip 50 is then inserted into the central cavity, and the tip 15 and the hub 30 are formed on opposite ends of the tube by conventional techniques. Alternatively, the dual-lumen tube can be co-extruded with a continuous reinforcing strip in the septum.

Figure 4:
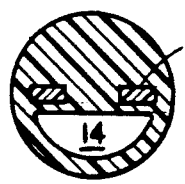
FIG. 4 is a section taken generally along line 4—4 in FIG. 2.
Figure 5:
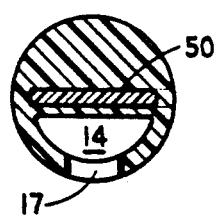
FIG. 5 is a section taken generally along line 5—5 in FIG. 2.

In the particular embodiment illustrated in FIGS. 1–6, the catheter tip 15 is molded as a unitary part of the catheter tube. This is accomplished by placing a tip mold around the distal end of the tube which forms the two D-shaped lumens, with the reinforcing strip in place and with mold inserts in place for forming the end of the intake lumen 13 and the extension of the return lumen 14 through the tip. As can be seen in FIGS. 2 and 4, the end portion of the reinforcing strip is preferably provided with a plurality of holes 51, 52 and 53 so that during the molding of the tip the molten silicone flows through the holes in the reinforcing strip (the entire distal end portion of the tube within the tip-forming mold is normally melted in this process). Then when the silicone is subsequently solidified, the reinforcing strip is locked firmly to the tip by the material that solidifies within the holes 51–53 of the strip. This interlocking of the reinforcing strip and the silicone holds the reinforcing strip securely in place, and ensures that the strip does not penetrate or separate through the relatively soft silicone tip during and after the insertion of the catheter.

At the proximal end of the catheter, the reinforcing strip 50 is similarly interlocked with the silicone that forms the hub 30. Thus, as can be seen in FIGS. 7 and 9, the proximal end of the strip 50 forms a hole 54 for receiving molten silicone during the in-situ molding of the hub 30. Then when the silicone solidifies, the strip 50 is securely interlocked with the hub 30.

To minimize kinking, the catheter of FIGS. 1–6 has a spiral 70 of relatively stiff material embedded in the cylindrical wall of the catheter along a substantial portion of the length of the catheter. The spiral 70 is preferably a thin metal wire wound helically around the extruded silicone tube, and then covered with a layer 71 of silicone so that the wire is not exposed to body tissue. The silicone is preferably applied as a liquid so that it flows around the spiral 70 and becomes a part of the silicone side walls of the catheter. If desired, a strong polymeric monofilament, e.g., nylon, may be used instead of the metal wire. The spiral 70 will always tend to retain its cylindrical shape, and thus also tends to hold the outer wall of the catheter in a cylindrical shape, thereby resisting kinking of the catheter. Consequently, the catheter can be bent, even at acute angles, without kinking. The use of such anti-kinking spirals in catheters is not new by itself, but the use of this feature in multiple-lumen silicone catheters such as those of the present invention leads to significant advantages in certain applications, as will be described in more detail below.

As shown in FIG. 1, a "Dacron" collar 75 is provided around the main body portion of the catheter to facilitate the growth of body tissues directly around the catheter where it enters the patient's body. The use of such a collar is well known in the catheter art.

FIGS. 11 and 12 illustrate a modified form of reinforcing member 80, which has a hollow D-shaped cross section, rather than the flat strip used in the embodiment of FIGS. 1–10. The D-shaped reinforcing member 80 is dimensioned to fit snugly within the intake lumen 13, with the distal end of the member 80 abutting the solid tip at the distal end of the lumen 13 (see FIG. 2). After the reinforcing member 80 has been inserted into the lumen 13, a thin layer 81 of silicone is formed on the inside walls of the member 80, e.g., by simply wicking a silicone liquid through the interior of the member 80 by capillary action. Thus, the wall of the lumen 13 is a multi-layer construction formed by the cylindrical body 11 and its septum 12, the reinforcing member 80, and the silicone layer 81.

If desired, the D-shaped reinforcing member 80 may be inserted into the intake lumen 13 only during insertion of the catheter into the patient. After the catheter is inserted, the reinforcing member 80 can be withdrawn from the catheter via the hub 30.

FIGS. 13–18 illustrate a catheter like the catheter of FIGS. 1–10 except that there is no reinforcing spiral around the outside wall of the catheter. This catheter is preferred for applications where kinking is not a problem, such as for implantation in the subclavian vein. The parts of the this catheter which are the same as those of the catheters of FIGS. 1–10 have been identified by the same reference numerals in FIGS. 13–18.

FIGS. 19–33 illustrate different configurations for the distal ends of catheters embodying this invention. Thus, the catheter of FIGS. 19–23 is made with a tapered conical tip 90 which is pre-molded and then inserted into the end of the extruded tube forming the two D-shaped lumens and the hollow septum. The reinforcing strip 50a in this embodiment is not apertured, but it extends slightly beyond the distal end of the cylindrical tube so as to fit into a mating slot formed in the pre-molded tip 90. The tip 90 also forms a D-shaped extension 91 which fits into the intake lumen and extends up to the edge of the first sidewall aperture, so as to form the terminus of the intake lumen. A shorter, hollow extension or "flash" 92 fits into the distal end of the return lumen, and is tapered to provide a smooth transition between the lumen of the cylindrical tube and the continuation of that lumen formed by the hollow tip. This pre-molded tip 90 is preferably made of silicone, and is bonded to the interior walls of the extruded tube by a silicone adhesive.

In the catheter of FIGS. 24–28, the intake lumen is terminated with an open end 100 by simply slicing off the distal portion of the lumen with a beveled cut. The return lumen continues all the way to the distal end of the tube, and retains the same D-shaped cross sectional configuration along its entire length. The reinforcing member 50b terminates in the region between the distal ends of the return lumen and the intake lumen, and the distal end portion of the hollow cavity formed by the septum is filled with a solid plug 101.

In the catheter of FIGS. 29–33, the intake lumen is terminated by an insert 110 which fills the distal end portion of the intake lumen formed by the extruded tube, from the distal end of the tube to the edge of the first sidewall aperture. The return lumen and the reinforcing member are exactly the same as in the catheter of FIGS. 24–28 described above.

One particularly advantageous application for the kink-resistant catheters of this invention is an improved long-term implantation technique for the femoral vein. In contrast to the subclavian vein, the femoral vein is readily accessible through the thigh and is well removed from critical organs such as the lungs and heart. Nevertheless, the femoral vein has not been a popular access site for hemodialysis catheters because of the higher risk of infection below the inguinal canal. With the kink-resistant catheters provided by the present invention, however, the catheter can extend downwardly from a point above the inguinal ligament through a subcutaneous tunnel, and then bent upwardly for insertion into the femoral vein. This method is illustrated in FIGS. 34-37.

The method for inserting the multi-lumen catheter 10 comprises the following steps: a lateral incision 120 of approximately a half inch is made percutaneously in the anterior abdominal wall. The incision 120 is made approximately 2-3 inches cephalad to the inguinal ligament. The distal end of the catheter 10 is inserted through the incision 120 by applying pressure on the proximal end of the catheter. The catheter is tunneled through the abdominal wall subcutaneously in a caudal direction toward the thigh. A second incision 121 of approximately a half inch is made approximately 1.75 inch below, that is, caudal to, the inguinal ligament. The catheter is pushed out of the body through the second incision 121 in the thigh at a distance of approximately 1.75 inch caudal to the inguinal ligament. In approximately that same region, the fascia is punctured with a percutaneous entry needle. The needle is introduced interiorly through the subcutaneous layers into the femoral vein 122. A flexible guide wire is introduced through the needle and advanced approximately 5-10 cm into the vessel. The needle is then withdrawn. The puncture formed by the needle is dilated using a small plastic tip on the end of a dilator, telescoped inside a peel-apart sheath 123. The dilator is inserted a short distance into the blood vessel and then removed. The multi-lumen catheter 10 which has been extruded from the skin of the thigh, is then threaded onto the guide wire in a cephalad direction and inserted interiorly through the sheath 123 into the femoral vein, in the direction of blood flow within the vein. The sheath 123 is removed by stripping it apart along the two longitudinal tear lines, and the guide wire is pulled out.

The catheter is then advanced in a cephalad direction until the loop protruding above the surface of the thigh is pulled beneath the skin. Both the incisions are then sutured, and the extension tubes of the catheters are connected to the dialysis circuit for hemodialysis.

In a further modified embodiment of the invention, the reinforcing member inside the catheter also provides a kink-resistant multi-lumen catheter. The preferred reinforcing member for this purpose is a T-shaped septum which resists kinking along a pair of mutually orthogonal transverse planes. Thus, in the embodiment of FIGS. 38-44, the septum includes not only the diametral wall 12 but also a radial wall 130 which is perpendicular to the wall 12. The radial wall 130 extends from the centerline of the diametral wall 12 along a radius of the catheter to the outer wall. The combination of the two Walls and 130 form three lumens 131, 132 and 133, one of which has a D-shaped transverse cross section. The D-shaped lumen 131 extends all the Way to the distal end of the catheter, while the other two lumens 132 and 133 terminate at different locations spaced longitudinally away from the distal end of the catheter. Sidewall apertures 134 and 135 open into the distal end of the lumen 132, and a similar pair of apertures 136 and 137 open into the distal end of the lumen 133.

In the preferred embodiment illustrated in FIGS. 38-44, the walls 12 and 130 are extruded simultaneously with the cylindrical tubular portion of the catheter so that all the silicone portions of the catheter are formed as a single unitary structure. Although the T-shaped septum is shown as solid silicone in FIG. 44, it will be understood that the T-shaped septum could be formed with a hollow interior for receiving a T-shaped nylon reinforcing member to provide still additional stiffness to the catheter.

The T-shaped septum also forms a triple-lumen catheter which is useful in certain critical-care applications where fluids are infused through one lumen (in this case the semi-circular lumen) while the other lumens are used for monitoring pressure, blood sampling, introducing medications and/or additional fluid infusions.

We claim:

1. A dual-lumen hemodialysis catheter comprising:
an elongated cylindrical tube made of a uniformly soft, elastic material which is compatible with the human body, said tube having an internal planar septum extending along the length thereof to form a pair of longitudinal lumens having distal openings which are offset from each other in the axial direction, and
a diametral reinforcing member extending along the length of said septum, and made of a material which is substantially stiffer than the material of said tube so that the catheter can be advanced longitudinally against a resistance by the application of force proximally of the resistance and so that said lumens will not collapse by deflection of said septum when the pressure differential of a dialysis system exists across said septum, said reinforcing member being completely embedded within said soft compatible material of said tube and septum so that said stiff reinforcing material is not exposed to blood passing through said lumens.

2. The dual-lumen catheter of claim 1 wherein said septum is flat so that said lumens have D-shaped cross sections.

3. The dual-lumen catheter of claim 1 which includes a hollow conical tip on the distal end of said tube, the outside surface of said conical tip merging smoothly with the outside surface of the tube, and the inside surface of said conical tip merging smoothly with the inside surface of one of said lumens, the distal end of the other of said lumens being longitudinally spaced from the distal end of said tip.

4. The dual-lumen catheter of claim 3 wherein said conical tip forms a solid connection from the distal end of said septum and other lumen to the distal end of said tip, and the distal end of said reinforcing member engages said solid connection providing axial column strength so that longitudinal forces applied to said tube are transmitted to said tip via said reinforcing member so as to apply to the tip of said catheter a longitudinal force which urges said catheter in the distal direction.

5. The dual-lumen catheter of claim 3 wherein said conical tip is molded directly onto the end of said tube.

6. The dual-lumen catheter of claim 3 wherein the distal end of one of said lumens and said septum are connected to said conical tip by solid material.

7. The dual-lumen catheter of claim 3 wherein said conical tip is preformed and bonded to the end of said tube, a portion of said preformed tip extending into said tube to form the terminus of one of said lumens.

8. The dual-lumen catheter of claim i wherein said reinforcing member is made of nylon.

9. The dual-lumen catheter of claim 1 wherein said reinforcing member and a portion of said tube at the distal end thereof are interlocked.

10. The dual-lumen catheter of claim 1 which includes a kink-resisting spiral of reinforcing material wound around a substantial length of said tube.

11. The dual-lumen catheter of claim 10 wherein said spiral is embedded in the cylindrical wall of said tube.

12. The dual-lumen catheter of claim 1 wherein said reinforcing member includes a planar stiff material enclosed within said septum.

13. The dual-lumen catheter of claim 1 which includes a circumferential reinforcing member extending around the circumference of said cylindrical tube.

14. A dual-lumen catheter comprising:

an elongated flexible cylindrical tube made of a uniformly soft material which is compatible with the human body, said tube having an internal planar septum extending along the length thereof to form a pair of longitudinal lumens having distal openings which are offset from each other in the axial direction, said septum comprising a pair of transversely spaced longitudinal webs formed as integral parts of said tube, and a reinforcing member comprising a flat strip of stiff material located longitudinally between said webs and bonded thereto so that said reinforcing member is completely enclosed by said webs of soft compatible material and is isolated from body fluids passing through said lumens, said reinforcing member extending along the length of said tube and being made of a material which is substantially stiffer than the material of said tube so that the catheter can be advanced longitudinally against a resistance by the application of force proximally of the resistance and so that said lumens will not collapse by deflection of said septum when a pressure differential exists across said septum.

15. The dual-lumen catheter of claim 14 wherein the transverse dimension of said reinforcing strip, in the direction parallel to said webs, is greater than the inside diameter of said tube so that said strip extends partially into the walls of the tube.

16. A method of introducing a dual-lumen catheter into a femoral vein of a patient for long-term use, said method comprising the steps of making a subcutaneous tunnel on the abdomen of the patient, beginning above the inguinal ligament and extending downwardly to a point on the thigh that is proximate the femoral vein, passing a dual-lumen catheter downwardly through said tunnel, and then bending the catheter and inserting it upwardly into said femoral vein, in the direction of blood flow within said vein, said catheter being bent in a generally U-shaped configuration between the lower end of the tunnel and the point of access to said femoral vein, said U-bend being reinforced by a spiral winding of reinforcing material.

17. A multiple-lumen catheter comprising:

an elongated cylindrical silicone tube having an internal planar septum extending along the length thereof to form a pair of longitudinal lumens having distal openings which are offset from each other in the axial direction.

one of said distal openings being formed by at least one aperture in the side wall of said tube opening into one of said lumens, and a reinforcing solid-walled tube extending along the full length of, and embedded in the walls of, only one of said lumens for transmitting forces applied to the proximal end of said tube to said conical tip, and for preventing one of said lumens from collapsing when the pressure differential of a dialysis system exists across said septum.

18. The dual-lumen catheter of claim 17 wherein both said one lumen and said reinforcing member have D-shaped transverse cross sections.

19. The dual-lumen catheter of claim 17 wherein the inside walls of said reinforcing member are coated with the same material that forms said tube so that said tubular reinforcing member is isolated from body tissues and fluids.

20. A dual-lumen catheter comprising:

an elongated cylindrical tube made of a uniformly soft, elastic material and having an internal planar septum extending along the length thereof to form a pair of longitudinal lumens having D-shaped cross sections and distal openings which are offset from each other in the axial direction, said septum comprising a flat strip of stiff material extending longitudinal through said septum, the distal end of said strip being connected to the distal end of said tube and having apertures therein, portions of said tube extending transversely through said apertures to interlock said strip and said tube, said reinforcing member extending along the length of said tube and being made of a material which is substantially stiffer than the material of said tube so that the catheter can be advanced longitudinally against a resistance by the application of force proximally of the resistance and so that said lumens will not collapse by deflection of said septum when the pressure differential of a dialysis system exists across said septum.

21. A blood purification system comprising:

a dialysis system for purifying a patient's blood; and a dual-lumen catheter coupled to said dialysis system comprising:

an elongated cylindrical tube made of a soft, elastic material which is compatible with the human body, said tube having an internal septum extending along the length thereof to form first and second longitudinal lumens having distal openings which are offset from each other in the axial direction, wherein said dialysis system withdraws blood through said first lumen under a negative pressure and returns blood through said second lumen under a positive pressure, so that a pressure differential exists across said septum, and a diametral reinforcing member extending along the length of said tube and made of a material which is substantially stiffer than the material of said tube so that the catheter can be advanced longitudinally against a resistance by the application of force proximally of the resistance and so that said first lumen will not collapse by deflection of said septum from the pressure differential produced across said septum by a dialysis system said reinforcing member being completely embedded within said soft compatible material of said tube and septum so that said stiff reinforcing material is not exposed to blood passing through said lumens.

22. A dual-lumen catheter comprising:

an elongated cylindrical tube made of a uniformly soft, elastic material which is compatible with the human body, said tube having an internal planar septum extending along the length thereof to form a pair of longitudinal lumens having distal openings which are offset from each other int he axial direction, and a diametral reinforcing strip extending along the length of said septum, said reinforcing strip being sufficiently stiffer than the material of said tube to prevent collapse of either of said lumens by a pressure differential across the reinforced septum, said reinforcing member being completely embedded within said soft compatible material of said tube and septum so that said stiff material of said reinforcing strip is not exposed to body fluids passing through said lumens.

23. A dual-lumen catheter comprising:

an elongated flexible cylindrical tube made of a soft polymer and having an internal planar septum extending axially therein to divide the interior of said tube into a pair of longitudinal lumens which are D-shaped in traverse section, one of said lumens extending through the distal end of the catheter, at least one aperture in the side wall of said tube opening into the other of said lumens, said septum comprising a pair of parallel webs joined to the side walls of said tube, and a diametral reinforcing strip enclosed between said webs, so that said strip is completely embedded within said septum so that said reinforcing material is not exposed to body fluids passing through said lumens, said strip having a greater stiffness than said tube and webs in the axial direction, and means for connecting the proximal ends of said lumens to two different fluid flow paths.

24. The dual-lumen catheter of claim 23 which includes a conically tapered tip whose circumference smoothly merges with the circumference of the catheter.

25. The dual-lumen catheter of claim 24 wherein the first lumen opens at the apex of the conically tapered tip.

26. The dual-lumen catheter of claim 24 wherein the tip of the catheter is attached to the distal end of said reinforcing member.

27. The dual-lumen catheter of claim 23 wherein said reinforcing member is enveloped in the catheter material on all the sides and ends.

28. The dual-lumen catheter of claim 23 wherein the proximal end of said reinforcing member is anchored at the lumen diversion portion of the catheter.

29. The dual-lumen catheter of claim 23 which includes additional spiral reinforcement along its circumference.

30. The dual-lumen catheter of claim 23 wherein said reinforcing member extends laterally beyond the internal diameter of the tube to anchor in the walls of the tube.

31. A dual-lumen hemodialysis catheter comprising:

an elongated cylindrical tube made of a uniformly soft, elastic material which is compatible with the human body, said tue having an internal planar septum extending along the length thereof to form a pair of longitudinal lumens having distal openings which are offset from each other in the axial direction, and a diametral reinforcing member extending along the length of said septum and made of a material which is substantially stiffer than the material of said tube, said reinforcing member being completely embedded within said soft compatible material of said tube and septum so that said stiff reinforcing material is not exposed to blood passing through said lumens.

32. A dual-lumen catheter comprising:

an elongated flexible cylindrical tube made of a uniformly soft material which is compatible with the human body, said tube having an internal planar septum extending along the length thereof to form a pair of longitudinal lumens having distal openings which are offset from each other int he axial direction, said septum comprising a pair of transversely spaced longitudinal webs formed as integral parts of said tube, and a reinforcing member comprising a flat strip of stiff material located longitudinally between said webs and bonded thereto so that said reinforcing member is completely enclosed by said webs of soft compatible material and is isolated from body fluids passing through said lumens, said reinforcing member extending along the length of said tube and being made of a material which is substantially stiffer than the material of said tube.

33. A blood purification system comprising:

a dialysis system for purifying a patient's blood; and a dual-lumen catheter coupled to said dialysis system comprising:

an elongated cylindrical tube made of a soft, elastic material which is compatible with the human body, said tube having an internal septum extending along the length thereof to form first and second longitudinal lumens having distal openings which are offset from each other in the axial direction, wherein said dialysis system withdraws blood through said first lumen under a negative pressure and returns blood through said second lumen under a positive pressure, so that a pressure differential exists across said septum, and a diametral reinforcing member extending along the length of said tue and made of a material which is substantially stiffer than the material of said tube, said reinforcing member being completely embedded within said soft compatible material of said tube and septum so that said stiff reinforcing material is not exposed to blood passing through said lumens.

34. A dual-lumen catheter comprising:

an elongated cylindrical tube made of a uniformly soft, elastic material which is compatible with the human body, said tube having an internal planar septum extending along the length thereof to form a pair of longitudinal lumens having distal openings which are offset from each other in the axial direction, and a diametral reinforcing strip extending along the length of said septum, and made of a material which is substantially stiffer than the material of said tube, said reinforcing member being completely embedded within said soft compatible material of said tube and septum so that said stiff material of said reinforcing strip is not exposed to body fluids passing through said lumens.

* * * * *